United States Patent
Wang et al.

(10) Patent No.: US 10,064,906 B2
(45) Date of Patent: Sep. 4, 2018

(54) METHOD OF PREPARING FERMENTED CRUDE EXTRACT HAVING ANGIOTENSIN CONVERTING ENZYME INHIBITING ACTIVITY

(71) Applicant: CHIA NAN UNIVERSITY OF PHARMACY & SCIENCE, Tainan (TW)

(72) Inventors: Shu-Chen Wang, Tainan (TW); Pin-Der Duh, Tainan (TW); Shih-Ying Chen, Tainan (TW); Chen-Kai Chang, Tainan (TW); Jung-Tsai Chen, Tainan (TW); Chih-Kuang Chiu, Tainan (TW)

(73) Assignee: Chia Nan University of Pharmacy & Science, Tainan (TW)

( * ) Notice: Subject to any disclaimer, the term of this patent is extended or adjusted under 35 U.S.C. 154(b) by 127 days.

(21) Appl. No.: 14/985,810

(22) Filed: Dec. 31, 2015

(65) Prior Publication Data

US 2017/0189461 A1    Jul. 6, 2017

(51) Int. Cl.

| | | |
|---|---|---|
| *A61K 36/185* | (2006.01) | |
| *A61K 36/28* | (2006.01) | |
| *A61K 36/899* | (2006.01) | |
| *A61K 36/21* | (2006.01) | |
| *A61K 36/48* | (2006.01) | |
| *A61K 36/55* | (2006.01) | |
| *A61K 36/23* | (2006.01) | |

(52) U.S. Cl.
CPC ............ *A61K 36/185* (2013.01); *A61K 36/21* (2013.01); *A61K 36/23* (2013.01); *A61K 36/28* (2013.01); *A61K 36/48* (2013.01); *A61K 36/55* (2013.01); *A61K 36/899* (2013.01); *A61K 2236/19* (2013.01)

(58) Field of Classification Search
CPC ............. A23V 2002/00; C07K 14/245; C07K 14/395; C07K 14/415; C12N 15/8243; C12N 15/8271; C12N 15/8273; C12N 9/2408; C12N 9/2414; C12N 9/2425; C12N 9/2428; C12N 9/96; C12N 9/2437; C12N 9/2445; Y02E 50/16; Y02E 50/17; Y02E 50/343; A23L 27/36; A23L 2/60; A23L 2/66; A23L 33/17; A23L 33/175; A23L 33/18; A23L 33/195; A23L 33/30; A23L 33/40; A23L 1/2366; A23L 2/06; A23L 2/54; A61K 38/00; A61K 38/10; A61K 38/16; A61K 38/164; A61K 38/168; A61K 38/17; A61K 38/1703; A61K 38/1709; A61K 38/1767; A61K 38/38; A61K 38/45; A61K 45/06; A61K 9/0053; A61K 9/0075; A61K 9/0095; A61K 9/146; A61K 9/2054; A61K 9/2866; A61K 2236/19; A61K 36/185; A61K 36/21; A61K 36/23; A61K 36/28; A61K 36/48; A61K 36/55; A61K 36/899; C12Y 207/04003; C12Y 302/01021; G01N 2500/00; G01N 33/6803; G01N 33/6806; G01N 33/6848; G06F 19/18; C12P 19/02; C12P 19/14; C12P 7/04; A21D 13/062; A21D 2/36

See application file for complete search history.

(56) References Cited

U.S. PATENT DOCUMENTS

| | | | | |
|---|---|---|---|---|
| 2008/0292750 A1* | 11/2008 | Baten | ..................... | A23C 9/127 426/43 |
| 2010/0189706 A1* | 7/2010 | Chang | ..................... | C12P 19/02 424/94.4 |
| 2011/0230394 A1* | 9/2011 | Wiatr | ..................... | A01N 31/02 514/2.4 |
| 2014/0206046 A1* | 7/2014 | Xu | .......................... | C12P 19/14 435/99 |

* cited by examiner

*Primary Examiner* — Lisa J Hobbs
(74) *Attorney, Agent, or Firm* — Rosenberg, Klein & Lee

(57) ABSTRACT

This invention is related to a method of preparing a fermented crude extract having angiotensin converting enzyme inhibiting activity. The method comprises the following steps. A material is dried, milled, and then mixed with water in a weight ratio of 1:11 to form a mixture solution. 0.1 vol % α-amylase is used to perform hydrolysis at 95° C. for 1 hour. 0.1 vol % glucoamylase is used to perform hydrolysis at 65° C. for 4 hours. A lactic acid bacterium is added in a culture medium containing the mixture solution to perform fermentation for 24 hours. The culture medium is centrifuged to take the supernatant thereof, and the supernatant is boiled for 20 minutes. The supernatant is filtered to obtain a fermented crude extract having angiotensin converting enzyme inhibiting activity.

8 Claims, 2 Drawing Sheets

METHOD OF PREPARING FERMENTED CRUDE EXTRACT HAVING ANGIOTENSIN CONVERTING ENZYME INHIBITING ACTIVITY

BACKGROUND

Field of Invention

This invention is related to a method of preparing a fermented crude extract having angiotensin converting enzyme (ACE) inhibiting activity. More particularly, this invention is related to a method of preparing a fermented crude extract by adding residue material in a culture medium for lactic acid bacteria fermentation. The fermented crude extract has ACE inhibiting ability.

Description of Related Art

Recently, hypertension has become one of common chronic diseases. Since hypertension may induce stroke and heart diseases, the hypertension patients need to take medicines to control the blood pressure. There are many causes of hypertension, wherein the angiotensin converting enzyme (ACE) plays one of the important roles. ACE can cause hypertension. Therefore, if the ACE activity can be inhibited, the blood pressure may be deceased. Currently in clinical, most people use chemical synthesized drug to inhibit the ACE activity to control the blood pressure, but these chemically synthesized drugs have many side effects. For example, long-term use of Renitec®, Tritace®, or Monopril® will easily cause dizziness, vomiting, fatigue, dry cough, high potassium, kidney failure and other phenomena. Therefore, if a better method of regulating blood pressure can be developed, it will be able to greatly enhance the well-being of hypertension patients.

Lactic acid bacteria (LAB) are bacteria that can metabolize sugars to produce lactic acid. These bacteria include *Lactobacillus, Streptococcus*, and *Leuconostoc*. LAB is also the most important group of probiotics to increase the amount of probiotics in the human body. Fermented milk, yogurt, and cheese fermented by LAB can inhibit ACE activity to decrease blood pressure. For increasing the amount of active ingredients inhibiting ACE in the liquid fermented by LAB, many researches tried to add natural materials in the culture medium for LAB fermentation. For example, "Studies on the Production Technology and Biological Activities of Lactic Acid Bacteria Fermented Oyster-Milk Food Product" (National Taiwan Ocean University, Yuarn-Yee Chang, 2004) used the residue of fresh oyster extracted by hot water, 1 wt % glucose, and 15 wt % skim milk reconstituted from skimmed milk powder to be fermented by LAB at 37° C. The fermented milk was used to perform ACE inhibiting test, and it was found to have better inhibiting effect on ACE. "Study on Angiotensin Converting Enzyme Inhibiting Activity of Chinese Herbal Medicines Extract Fermented by Lactic Acid Bacteria" (Southern Taiwan University of Science and Technology, Che-Cheng Yang, 2009) used different extracting ratios, temperatures, and times to extract *Gastrodia elata, Scutellariae radix, Mesona chinensis*, and the extracting solutions were fermented by LAB to effectively increase the original blood pressure decreasing effect. "Studies on ACE-inhibiting activity of lactic acid bacteria fermented sake lees" (TaTung University, Shu-Wen Cheng, 2011) used a LAB strain screened by pickles fermentation product. This LAB strain was used to ferment the sake lees on a small scale. The ACE activity inhibiting effect was measure after 12-hour fermentation. The results showed that all have inhibiting ability of ACE activity.

However, the choices for materials that can be added into mediums for LAB fermentation are still limited. How to find out more materials that can be used to increase the effective ingredient inhibiting ACE activity and develop better healthcare products or medical compositions to control blood pressure is the research direction of the inventors of this invention.

SUMMARY

A main object of this invention is to provide a method of preparing a fermented crude extract. This method is a method of adding dregs materials into a culture medium for lactic acid bacteria fermentation to prepare a fermented crude extract having angiotensin converting enzyme inhibiting activity.

To reach the object above, this invention provides a method of preparing a fermented crude extract having angiotensin converting enzyme inhibiting activity. The method comprises the following steps. Step 1: A material is dried, milled, and then mixed with water in a weight ratio of 1:11 to form a mixture solution. Step 2: 0.1 vol % α-amylase is added in the mixture solution to perform hydrolysis at 95° C. for 1 hour. Step 3: 0.1 vol % glucoamylase is added in the mixture solution to perform hydrolysis at 65° C. for 4 hours. Step 4: 1% (w/w) of a lactic acid bacterium is added in a culture medium containing the mixture solution to perform fermentation for 24 hours. Step 5: The culture medium is centrifuged to take the supernatant thereof, and the supernatant is boiled for 20 minutes. Step 6: The supernatant is filtered to obtain a fermented crude extract having angiotensin converting enzyme inhibiting activity.

In one embodiment of this invention, the material is selected from a group consisting of sunflower seeds, wheat, red quinoa, peanut residue, linseed residue, carrot, sesame residue, red beans, green beans, millet, black beans, purple sweet potato, and more preferably from a group consisting of carrot, sesame residue, linseed residue, and millet.

In one embodiment of this invention, a pH value of the mixture solution in the step 3 has been adjusted to pH 4.5. The lactic acid bacterium in the step 4 has been cultured for 24 hours, and the fermentation in step 4 has been performed at 35-37° C. and rotated at 70-80 rpm for 24 hours.

In one embodiment of this invention, the culture medium in step 4 is prepared by the following steps. (a) A sugar-free soymilk is sterilized at 121° C. for 15 minutes. (b) The soymilk is diluted by water to a protein concentration of 16 mg/mL. (c) 2 wt % glucose is added to the soymilk according to the diluted volume thereof, as well as the soymilk is then sterilized at 121° C. for 5 minutes and then cooled for ready to use.

In one embodiment of this invention, the culture medium in step 5 is centrifuged at a speed of 8,000-10,000 rpm for 10-15 minutes.

In one embodiment of this invention, the supernatant in step 6 is filtered by a 0.45 µm filter.

In light of foregoing, the fermented crude extract of this invention has angiotensin converting enzyme inhibiting activity, and thus can be further used in a medical or a health-care composition.

DETAILED DESCRIPTION

The objects and structural functional advantages of this invention will be illustrated according to the structures shown in the figures with the embodiments below to make the Examiner have deeper and more specific understandings to this invention.

Figure 1:
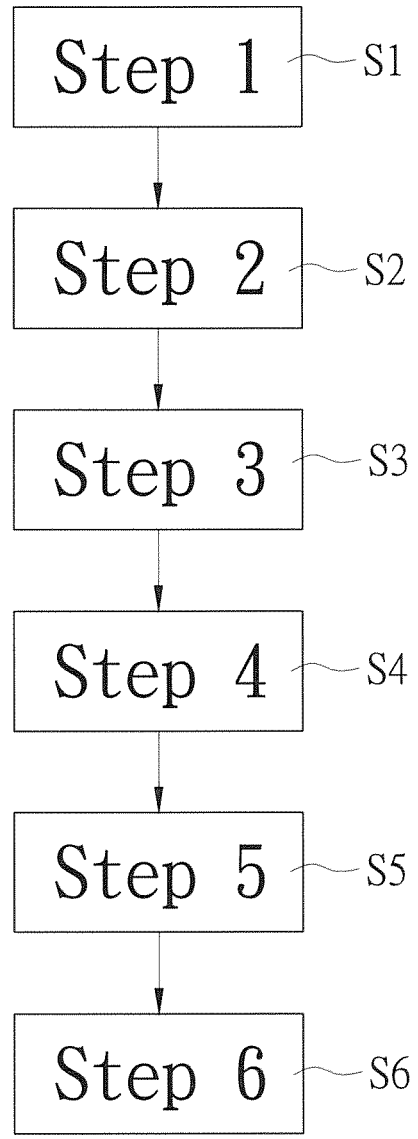
FIG. 1 is a step flowchart according to one preferred embodiment of this invention.

Please refer to FIG. 1, a method of preparing a fermented crude extract having angiotensin converting enzyme inhibiting activity in this invention comprises the following steps.

Step 1 (S1) A material is dried, milled, and then mixed with water in a weight ratio of 1:11 to form a mixture solution. The material is selected from a group consisting of sunflower seeds, wheat, red quinoa, peanut residue, linseed residue, carrot, sesame residue, red beans, green beans, millet, black beans, purple sweet potato, and more preferably from a group consisting of carrot, sesame residue, linseed residue, and millet.

Step 2 (S2): 0.1 vol % α-amylase is added in the mixture solution to perform hydrolysis at 95° C. for 1 hour.

Step 3 (S3): The pH value of the mixture solution is adjusted to pH 4.5, and 0.1 vol % glucoamylase is then added in the mixture solution to perform hydrolysis at 65° C. for 4 hours.

Step 4 (S4): 1% (w/w) of a lactic acid bacterium (preferably has been cultured for 24 hours) is added in a culture medium containing the mixture solution to perform fermentation for 24 hours (preferably at 35-37° C. and rotated at 70-80 rpm for 24 hours). The culture medium is prepared by the following steps. (a) A sugar-free soymilk is sterilized at 121° C. for 15 minutes. (b) The soymilk is diluted by water to a protein concentration of 16 mg/mL. (c) 2 wt % glucose is added to the soymilk according to the diluted volume thereof, as well as the soymilk is then sterilized at 121° C. for 5 minutes and then cooled for ready to use.

Step 5 (S5): The culture medium is centrifuged (such as at a speed of 8,000-10,000 rpm for 10-15 minutes) to take the supernatant thereof, and the supernatant is boiled for 20 minutes.

Step 6 (S6): The supernatant is filtered (such as by a 0.45 μm filter) to obtain a fermented crude extract having angiotensin converting enzyme inhibiting activity to be further used for adjusting blood pressure.

Furthermore, the embodiments below can be used to prove the actual applied scope of this invention but does not intend to limit the scoped of this invention.

<Material Preparation>

The sunflower seeds, wheat, red quinoa, peanut residue, linseed residue, carrot, and sesame residue were dried and milled into powder. The powder and water is mixed in a ratio of 1:11. 0.1 vol % α-amylase is added in the mixture solution to perform hydrolysis at 95° C. for 1 hour. The pH value of the mixture solution is adjusted to pH 4.5, and 0.1 vol % glucoamylase is then added in the mixture solution to perform hydrolysis at 65° C. for 4 hours.

<Soymilk Medium for Lactic Acid Bacteria>

The soymilk medium was a commercial sugar-free soymilk from Imei Food. The soymilk was sterilized at 121° C. for 15 minutes and then diluted by RO water to a protein concentration of 16 mg/mL. 2 wt % glucose is added to the soymilk according to the final prepared volume thereof. The soymilk is then sterilized at 121° C. for 5 minutes and then cooled for ready to use.

<Sources of Lactic Acid Bacteria>

The isolates of the lactic acid bacteria (LABs) were B0014, B0015, B0059, B0060, B0096, and B0137 listed in Table 1 below.

TABLE 1

| The nucleic acid sequence similarity of 16S rDNA of the lactic acid bacteria isolates. | | |
|---|---|---|
| LAB isolates | Strain | Gene bank acc. No. | Sequence similarity (%) |
| B0014 | Lactobacillus casei | NC_008526.1 | 99 |
| B0015 | Lactobacillus casei | NC_008526.1 | 99 |
| B0059 | Lactobacillus casei | NC_008526.1 | 99 |
| B0060 | Lactobacillus casei | NC_008526.1 | 99 |
| B0096 | Lactobacillus plantarum | NC_004567.2 | 99 |
| B0137 | Lactobacillus casei | NC_008526.1 | 99 |

<Fermentation and Preparation>

1 mL of activated broth containing LAB cultured for 24 hours was added to the soymilk medium above, and different mixture solutions of prepared materials were respectively added to the soymilk medium. The LABs were cultured at 35° C. and shaken (80 rpm/min) for 24 hours. The cultured LAB fermentation solutions were placed in sterilized centrifuge tube and centrifuged at 8,000 rpm for 15 minutes. The supernatant was cooked in boiling water for 20 minutes, and then filtered by a 0.45 μm filter. The ACE inhibiting ability of the filtered supernatant was measured.

<ACE Inhibiting Ability Measurement>

(1) Drug Preparation

Hippuryl-histidyl-leucine (HHL) was prepared. Potassium phosphate buffer solution containing 0.3 M NaCl was used to dissolve HHL (Sigma, MO, US), and the HHL concentration was 5 mM. ACE was prepared. Potassium phosphate buffer solution containing 50 vol % glycerol was used to dissolve ACE (Sigma, MO, US), and the ACE concentration was 143 mU/mL.

(2) Pyridine-Benzene Sulfonyl Chloride (BSC) Colorimetry

9 μL of 0.2 M potassium phosphate buffer solution (pH 8.2) containing 0.3 M NaCl, 15 μL of matrix HHL and 6 μL of sample were added, and 30 μL of ACE was finally added. The total volume was 60 μL. After in 37° C. water bath for 1 hour, 50 μL of 1 N NaOH solution was added to terminate the reaction. Afterwards, 100 μL of a coloring agent, pyridine, and 50 μL of BSC were added. After uniformly shaking, the mixture was placed on ice and cooled down to room temperature. 200 μL was placed in a 96-well plate, absorbance at 410 nm was measured by a spectrophotometer. Inhibiting percentage was calculated by the formula below:

$$[(A-B)-(C-D)]/(A-B) \times 100\%$$

A is the absorbance of the blank without containing samples, B is the absorbance of the blank without containing samples and using buffer solution to replace ACE, C is the absorbance of samples, and D is the absorbance of samples using the buffer solution to replace the ACE.

(3) Reverse Phase-High Performance Liquid Chromatography (RP-HPLC)

9 μL of 0.2 M potassium phosphate buffer solution (pH 8.2) containing 0.3 M NaCl, 15 μL of matrix HHL and 6 μL of sample were added, and 30 μL of ACE was finally added. The total volume was 60 μL. After in 37° C. water bath for 1 hour, 50 μL of 1 N NaOH solution was added to terminate the reaction. Afterwards, 10 μL was taken to be injected into a C18 column to measure hippuric acid (HA), which is the product of ACE. The eluent was 50 vol % methanol containing 0.01 vol % trichloroacetic acid (TCA), and HA was detected by UV 228 mm. Various concentrations of HA were used as standards, and the concentrations and absorbance thereof were plotted to obtain a regression equation. The inhibiting rate was calculated by the following formula using the calculated HA content. The inhibiting percentage was calculated as follow:

$$[(A-B)-(C-D)]/(A-B)\times100\%$$

A is the HA content without adding samples, B is the blank and using a buffer solution to replace ACE, C is the HA content added with samples, and D is the HA content added with samples and using a buffer solution to replace ACE.

Figure 2:
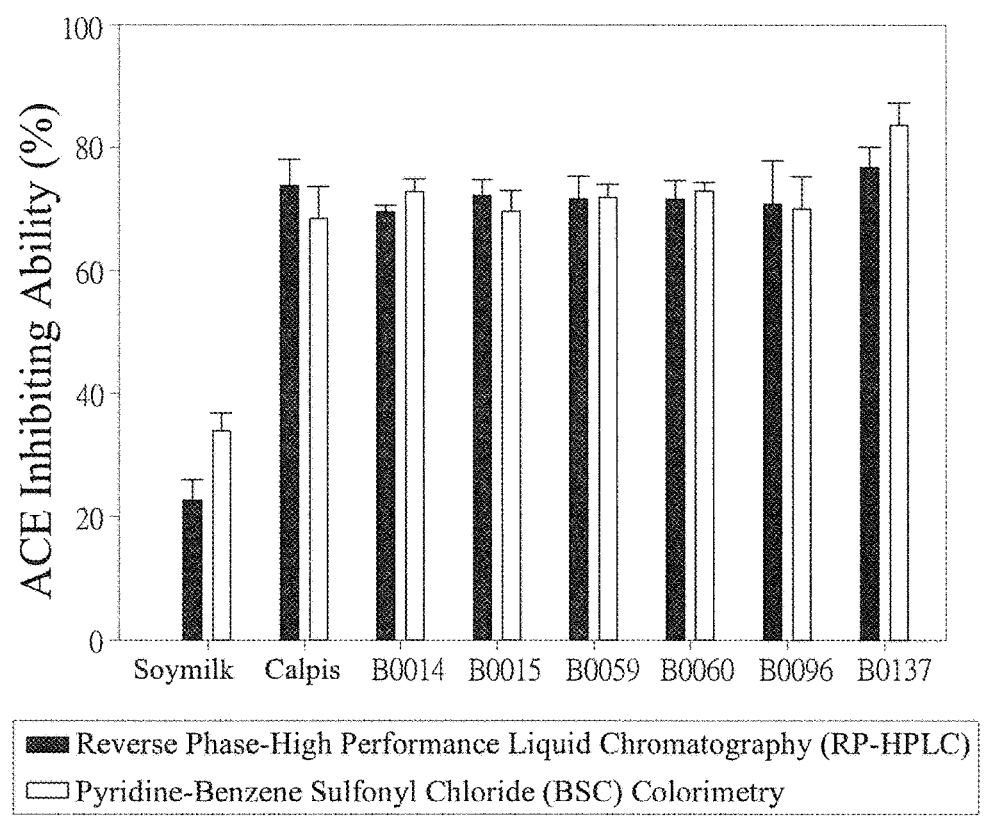
FIG. 2 is a diagram analyzing the effect of the fermented crude extract of the lactic acid bacteria on ACE.

The inhibiting ability of the LAB fermented crude extract on ACE was analyzed, and the ACE inhibiting abilities measured by RP-HPLC and BSC colorimetry were compared. The control group was soymilk without adding LAB. The positive control group was Calpico. The results are shown in FIG. 2. The fermented crude extracts of LABs all have ACE inhibiting ability, and the results measured by the two methods are the same. Therefore, the BSC colorimetry was used to measure the ACE inhibiting ability afterwards.

Embodiment 1: Analyzing the Effects of Fermented Crude Extract Using Different Materials on ACE Different concentrations (20 wt % and 40 wt %) of sunflower seeds, wheat, red quinoa, peanut residue, linseed residue, carrot, and sesame residue were added into the soymilk medium to perform fermentation by LAB. Next, the ACE inhibiting ability of different fermented crude extract was analyzed. The control group was the material not added by LAB strains. N.D. means "not detected." The results are shown in Table 2. Comparing with the control group, all of the 20 wt % and 40 wt % materials had good ACE inhibiting ability, wherein the 20 wt % red quinoa, 20 wt % linseed residue, 20 wt % sesame residue, and 40 wt % carrot had better ACE inhibiting rate.

TABLE 2

| Materials | LAB Strain | LAB No. (log CFU/mL) | ACE Inhibiting Ability (%) |
|---|---|---|---|
| 40 wt % sunflower seeds | control group | N.D. | 72.77 ± 0.36 |
| | B0096 | 9.63 | 84.98 ± 4.36 |
| 20 wt % sunflower seeds | control group | N.D. | 64.41 ± 2.29 |
| | B0096 | 9.60 | 81.69 ± 1.62 |
| 40 wt % wheat | control group | N.D. | 65.01 ± 4.50 |
| | B0096 | 9.61 | 67.30 ± 2.30 |
| 20 wt % wheat | control group | N.D. | 56.20 ± 3.37 |
| | B0096 | 9.62 | 77.85 ± 1.36 |
| 40 wt % red quinoa | control group | N.D. | 53.33 ± 0.94 |
| | B0096 | 9.46 | 84.75 ± 0.77 |
| 20 wt % red quinoa | control group | N.D. | 44.61 ± 5.03 |
| | B0096 | 9.61 | 85.91 ± 1.58 |
| 40 wt % peanut residue | control group | N.D. | 54.86 ± 0.31 |
| | B0096 | 9.56 | 81.47 ± 0.26 |
| 20 wt % peanut residue | control group | N.D. | 47.89 ± 1.35 |
| | B0096 | 9.49 | 77.52 ± 1.69 |
| 40 wt % linseed residue | control group | N.D. | 49.67 ± 3.082 |
| | B0096 | 9.72 | 74.96 ± 1.20 |
| 20 wt % linseed residue | control group | N.D. | 51.01 ± 0.70 |
| | B0096 | 9.732 | 84.88 ± 2.00 |
| 40 wt % carrot | control group | N.D. | 48.37 ± 2.35 |
| | B0096 | 9.562 | 87.55 ± 1.83 |
| 20 wt % carrot | control group | N.D. | 54.05 ± 1.51 |
| | B0096 | 9.65 | 79.48 ± 0.22 |

TABLE 2-continued

| Materials | LAB Strain | LAB No. (log CFU/mL) | ACE Inhibiting Ability (%) |
|---|---|---|---|
| 40 wt % sesame residue | control group | N.D. | 74.89 ± 3.18 |
| | B0096 | 9.73 | 85.74 ± 1.75 |
| 20 wt % sesame residue | control group | N.D. | 63.76 ± 2.96 |
| | B0096 | 9.68 | 92.15 ± 3.38 |

Embodiment 2: Analyzing the Effects of Fermented Crude Extracts from Different LAB Strains Using Different Materials on ACE The materials had higher ACE inhibiting ability in Embodiment 1 (20 wt % red quinoa, 20 wt % linseed residue, 20 wt % sesame residue, and 40 wt % carrot) were chosen to test the effects of fermented crude extracts from different LAB strains (B0014, B0015, B0059, B0060, B0096, and B0137) on ACE. The results are shown in Tables 3-6. The chosen 4 materials were added into the soymilk medium, and different LAB strains were used to perform fermentation to obtain fermented crude extracts. The obtained fermented crude extracts all had ACE inhibiting effect, and the inhibiting rates are all higher than 70%.

TABLE 3

| Materials | LAB Strain | LAB No. (log CFU/mL) | ACE Inhibiting Ability (%) |
|---|---|---|---|
| 20 wt % red quinoa | control group | N.D. | 46.01 ± 1.87 |
| | B0014 | 9.60 | 92.06 ± 2.05 |
| | B0015 | 9.63 | 87.15 ± 2.43 |
| | B0059 | 9.57 | 87.28 ± 1.71 |
| | B0060 | 9.60 | 89.24 ± 1.27 |
| | B0096 | 9.61 | 87.62 ± 1.98 |
| | B0137 | 9.57 | 88.22 ± 1.84 |

TABLE 4

| Materials | LAB Strain | LAB No. (log CFU/mL) | ACE Inhibiting Ability (%) |
|---|---|---|---|
| 20 wt % linseed residue | control group | N.D. | 51.02 ± 0.70 |
| | B0014 | 9.71 | 82.58 ± 1.36 |
| | B0015 | 9.61 | 82.37 ± 2.10 |
| | B0059 | 9.64 | 82.95 ± 1.13 |
| | B0060 | 9.66 | 86.38 ± 1.63 |
| | B0096 | 9.77 | 84.88 ± 2.00 |
| | B0137 | 9.60 | 93.40 ± 1.90 |

TABLE 5

| Materials | LAB Strain | LAB No. (log CFU/mL) | ACE Inhibiting Ability (%) |
|---|---|---|---|
| 20 wt % sesame residue | control group | N.D. | 63.76 ± 2.96 |
| | B0014 | 9.36 | 82.01 ± 0.33 |
| | B0015 | 9.26 | 76.48 ± 1.74 |
| | B0059 | 9.44 | 72.20 ± 1.98 |
| | B0060 | 9.44 | 72.87 ± 1.35 |
| | B0096 | 9.68 | 92.15 ± 3.38 |
| | B0137 | 9.35 | 82.50 ± 1.47 |

TABLE 6

| Materials | LAB Strain | LAB No. (log CFU/mL) | ACE Inhibiting Ability (%) |
|---|---|---|---|
| 40 wt % carrot | control group | N.D. | 50.03 ± 0.70 |
| | B0014 | 9.37 | 82.17 ± 2.46 |
| | B0015 | 9.30 | 89.28 ± 1.52 |
| | B0059 | 9.40 | 92.63 ± 2.09 |
| | B0060 | 9.43 | 87.24 ± 1.06 |
| | B0096 | 9.43 | 90.88 ± 2.27 |
| | B0137 | 9.56 | 87.50 ± 1.47 |

TABLE 7

| Animal groups | Fed material | dose/day | Animal No (male rat) |
|---|---|---|---|
| blank | RO water | 10 mL/kg bw | 8 WKY rats |
| Control group | RO water | 10 mL/kg bw | 8 SHR rats |
| Positive control group | Calpis | 20.7 mL/kg bw | 8 SHR rats |
| B96 group | B96 | 1.03 g/kg bw | 8 SHR rats |
| B96SR group | B96SR | 1.03 g/kg bw | 8 SHR rats |

TABLE 8

| Animal groups | systolic blood pressure | | | |
|---|---|---|---|---|
| | 0 week | 2 weeks | 4 weeks | 6 weeks |
| blank | 126.0 ± 3.2 | 140.1 ± 2.5 | 138.5 ± 2.2 | 137.6 ± 1.7 |
| Control group | 175.1 ± 4.0 # | 190.3 ± 3.0 # | 208.1 ± 3.6 # | 208.9 ± 2.1 # |
| Positive control group | 165.5 ± 2.9 | 176.9 ± 3.8 | 184.3 ± 1.8 * | 187.5 ± 1.7 * |
| B96 group | 170.7 ± 1.8 | 185.4 ± 4.5 | 204.0 ± 2.9 | 189.1 ± 1.6 * |
| B96SR group | 175.2 ± 2.8 | 179.2 ± 3.2 | 184.1 ± 2.6 * | 186.2 ± 3.5 * |

In summary, using residue materials of sunflower seeds, wheat, red quinoa, peanut residue, linseed residue, carrot, sesame residue, red beans, green beans, millet, black beans, and purple sweet potato for fermentation indeed can obtain fermented crude extracts having ACE inhibiting activity. Moreover, different materials also can be further mixed together to be added into a culture medium to reach better ACE inhibiting effect.

Embodiment 3: Animal Test

Spontaneously hypertensive rats (SHR) and normal rats (Wistar Kyoto, WKY) were used to perform animal test by feeding with different LAB-fermented crude extracts to observe the effects on the systolic blood pressure. The experimental groups are shown in Table 7. Blank was WKY rats fed by water. Control group was SHR rats fed with water. The positive control group was SHR rats fed with Caplis and a product having blood-pressure regulating function from Japan. B96SR group was SHR rats fed with freeze-dried powder of crude extract fermented by B0096 LAB strains using sesame residue. The weight and the food intake of SHR rats were not affected by the various experimental materials. The results are shown in Table 8. Symbol # represents significant difference compared with the blank. Symbol * represents significant difference (p<0.05, Dunnett's test, 2-sides) compared with the control group. The blood pressure measuring results showed that the blood pressure of B96SR group was decreased by 24.0 mmHg in the fourth week and the blood pressure of the B96 group was decreased 19.8 mmHg in the sixth week. The results all had significant difference (p<0.05) in statistics. Therefore, it can be determined that the tested materials had ACE inhibiting effects and achieve the blood pressure decreasing effect.

In addition, subacute toxicity test was performed. According to the tested material's solubility to put the greatest amount. The greatest powder solubility of the LAB strains B96, B96SR, B96E and E was 0.50, 0.50, 0.30, and 0.25 g/mL, respectively. The largest feeding volume of rats at one time was 10 mL/kg bw. Therefore, the doses of B96, B96SR, B96E and E for rats were 5.0, 5.0, 3.0, and 2.5 g/kg bw. Assumed that the dose was 30 times of the suggested amount for humans, and the suggested amount for humans was thus 0.17, 0.17, 0.10, and 0.08 g/kg bw. When the subacute toxicity test of rats was performed, the SHR rats (6 males and 6 females) were respectively fed with LAB products of B96 (5 g/kg bw/day), B96SR (5 g/kg bw/day), B96E (3.0 g/kg bw/day), and E (2.5 g/kg bw/day) for consecutive 28 days to observe the toxicity effect thereof. The results are shown in Table 9. All groups were survived, and no experimental animals show clinical toxicity symptoms during the test period. In addition, no significant difference occurred in the body weight increasing ratio and the feed consumption among the experimental groups and control groups, and the biochemical analysis of the blood and serum showed that the values were all in the scope of the normal background.

TABLE 9

| | | Groups | | | | |
|---|---|---|---|---|---|---|
| Analysis items | | blank | B96 | B96SR | E | B96E |
| Female | Death No/Total No | 0/6 | 0/6 | 0/6 | 0/6 | 0/6 |
| | Death rate (%) | 0 | 0 | 0 | 0 | 0 |
| Male | Death No/Total No | 0/6 | 0/6 | 0/6 | 0/6 | 0/6 |
| | Death rate (%) | 0 | 0 | 0 | 0 | 0 |

According to the embodiments above, it can be known that this invention has the following advantages compared with the existing technology:

1. In this invention, natural materials were added into culture mediums used for LAB fermentation to obtain fermented crude extracts having ACE inhibiting effects. The fermented crude extracts can be further used for blood-pressure regulating health-care products or medical products. The side effects of chemical synthesized drugs can thus be avoided.

2. In this invention, many residue materials were used for fermentation tests. It was found that many materials had very good ACE inhibiting ability. Therefore, the materials can be mixed and used according to the needs of practitioners to reach the better ACE inhibiting effect.

The figures and illustrations above are only used for preferred embodiments of this invention, and not used to limit the scope of this invention. Persons skilled in the art can vary or modify the embodiments above to have equal effect, and these variations and modifications should be viewed as in the scope of this invention.

What is claimed is:

1. A method of preparing a fermented crude extract having angiotensin converting enzyme inhibiting activity, comprising:
   (step 1) drying and milling a material, and then mixing the material with water in a weight ratio of 1:11 to form a mixture solution, wherein the material is selected from a group consisting of sunflower seeds, red quinoa, peanut residue, linseed residue, carrot, and sesame residue;
   (step 2) adding 0.1 vol % α-amylase in the mixture solution to perform hydrolysis at 95° C. for 1 hour;
   (step 3) adding 0.1 vol % glucoamylase in the mixture solution to perform hydrolysis at 65° C. for 4 hours;
   (step 4) adding 1% (w/w) of a lactic acid bacterium in a culture medium containing the mixture solution to perform fermentation for 24 hours, wherein the lactic acid bacterium is *Lactobacillus casei* or *Lactobacillus plantarum*;
   (step 5) centrifuging the culture medium to take a supernatant thereof and boiling the supernatant for 20 minutes;
   (step 6) filtering the supernatant and collecting the supernatant liquid passed through a filter to remove unwanted elements to obtain the fermented crude extract; and
   (step 7) measuring the angiotensin converting enzyme inhibiting activity of the fermented crude extract.

2. The method of claim 1, wherein the material is selected from carrot, sesame residue, linseed residue, and red quinoa.

3. The method of claim 1, wherein a pH value of the mixture solution in the step 3 has been adjusted to pH 4.5.

4. The method of claim 1, wherein the lactic acid bacterium in the step 4 has been cultured for 24 hours.

5. The method of claim 1, wherein the fermentation in step 4 is performed at 35-37° C. and rotated at 70-80 rpm for 24 hours.

6. The method of claim 1, wherein the culture medium in step 4 is prepared by a method comprising:
   (a) sterilizing a sugar-free soymilk at 121° C. for 15 minutes;
   (b) diluting the soymilk by water to a protein concentration of 16 mg/mL; and
   (c) adding 2 wt % glucose to the soymilk according to a diluted volume thereof, sterilizing the soymilk at 121° C. for 5 minutes, and then cooling the soymilk for ready to use.

7. The method of claim 1, wherein the culture medium in step 5 is centrifuged at a speed of 8,000-10,000 rpm for 10-15 minutes.

8. The method of claim 1, wherein the supernatant in step 6 is filtered by a 0.45 μm filter.

* * * * *